United States Patent [19]

Konopka et al.

[11] Patent Number: 4,755,173
[45] Date of Patent: Jul. 5, 1988

[54] SOFT CANNULA SUBCUTANEOUS INJECTION SET

[75] Inventors: April A. Konopka, Northridge; Peter C. Lord, Valencia, both of Calif.

[73] Assignee: Pacesetter Infusion, Ltd., Sylmar, Calif.

[21] Appl. No.: 58,067

[22] Filed: Jun. 4, 1987

Related U.S. Application Data

[63] Continuation-in-part of Ser. No. 834,173, Feb. 25, 1986, abandoned.

[51] Int. Cl.⁴ .............................................. A61M 5/00
[52] U.S. Cl. ................................. 604/167; 604/122; 604/180; 128/DIG. 26
[58] Field of Search .......... 604/51, 117, 122, 164–180; 128/DIG. 26

[56] References Cited

U.S. PATENT DOCUMENTS

| | | | |
|---|---|---|---|
| 2,238,323 | 4/1941 | Hollingsworth | 604/117 |
| 3,030,953 | 4/1962 | Koehn | 604/168 X |
| 3,547,119 | 12/1970 | Hall et al. | 604/180 X |
| 3,683,911 | 8/1972 | McCormick | 604/180 |
| 3,739,778 | 6/1973 | Monestere et al. | 604/167 |
| 3,853,127 | 12/1974 | Spademan | 604/167 |
| 3,860,006 | 1/1975 | Patel | 604/180 X |
| 3,919,724 | 11/1975 | Sanders et al. | 604/175 |
| 4,040,427 | 8/1977 | Winnie | 604/180 |
| 4,235,234 | 11/1980 | Whitney et al. | 604/177 X |
| 4,311,137 | 1/1982 | Gerard | 604/122 X |
| 4,430,081 | 2/1984 | Timmermans | 604/167 X |
| 4,645,495 | 2/1987 | Vaillancourt | 604/117 |

*Primary Examiner*—Dalton L. Truluck
*Attorney, Agent, or Firm*—Leslie S. Miller; Bryant R. Gold

[57] ABSTRACT

An injection set for delivering a fluid to a subcutaneous injection location in a patient is disclosed which has a soft cannula projecting from a bottom surface of a holding pad. An insertion needle is initially inserted through a septum located between a catheter hub and a retaining cap mounted on the holding pad. The insertion needle extends through a fluid chamber defined by the septum and the catheter hub and then through a lumen of the soft cannula, with the sharpened tip of the insertion needle extending beyond the end of the soft cannula when the insertion needle is fully inserted. The insertion needle, which allows priming of the injection set, may be removed following installation of the injection set without kinking of the soft catheter, and fluid may be supplied to the injection set for delivery to the patient.

23 Claims, 5 Drawing Sheets

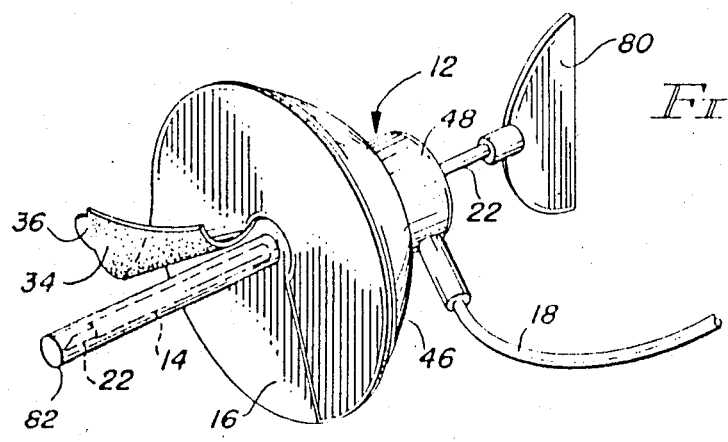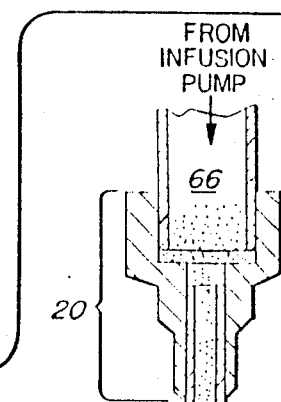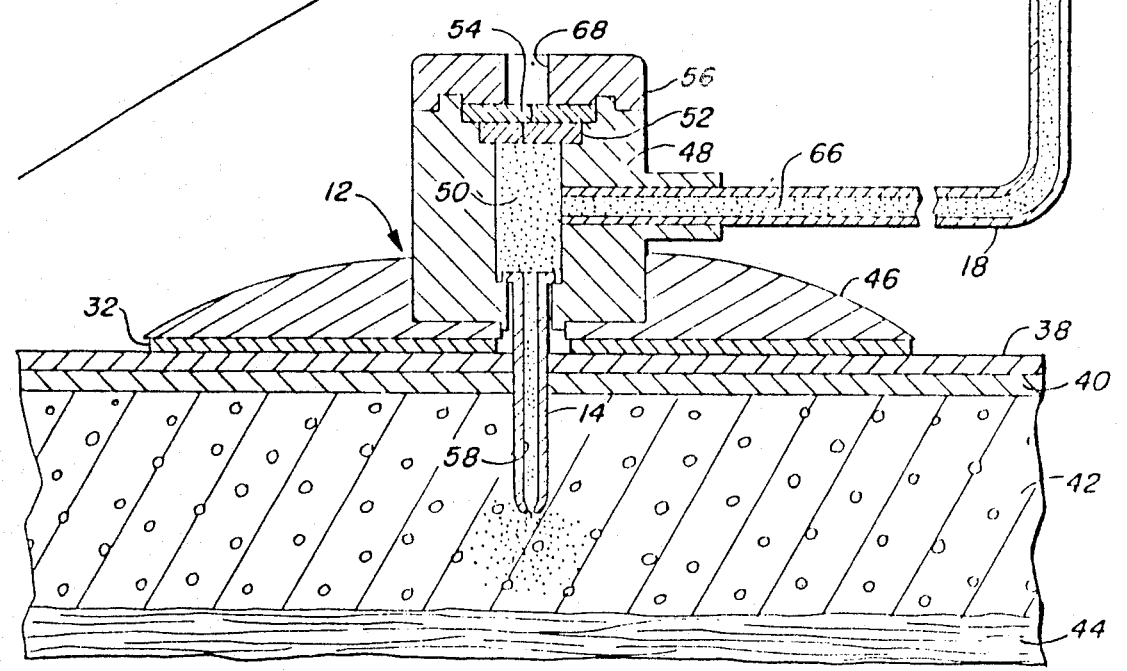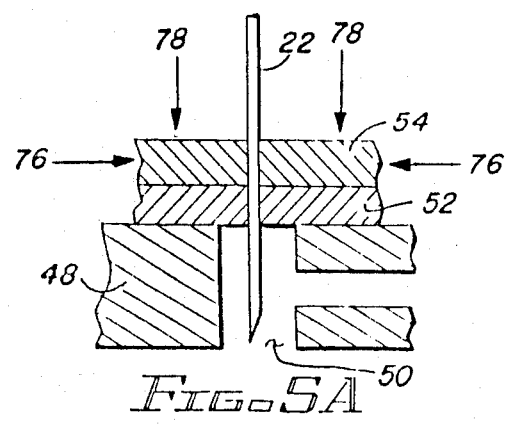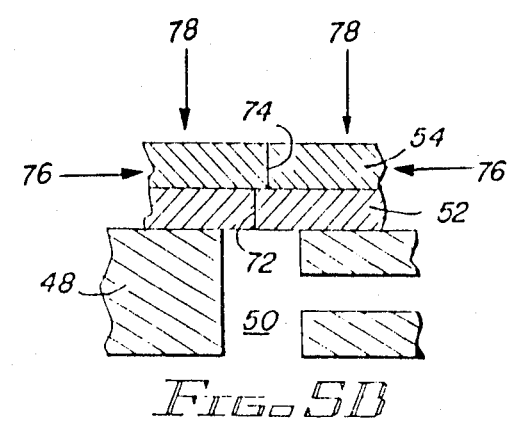

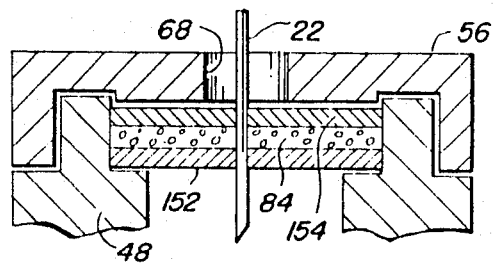
_FIG=7A_
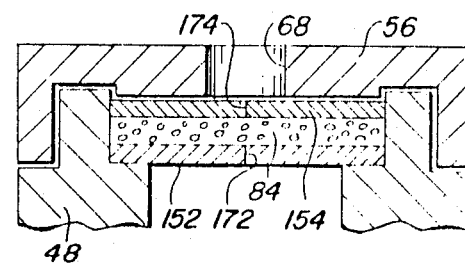
_FIG=7B_
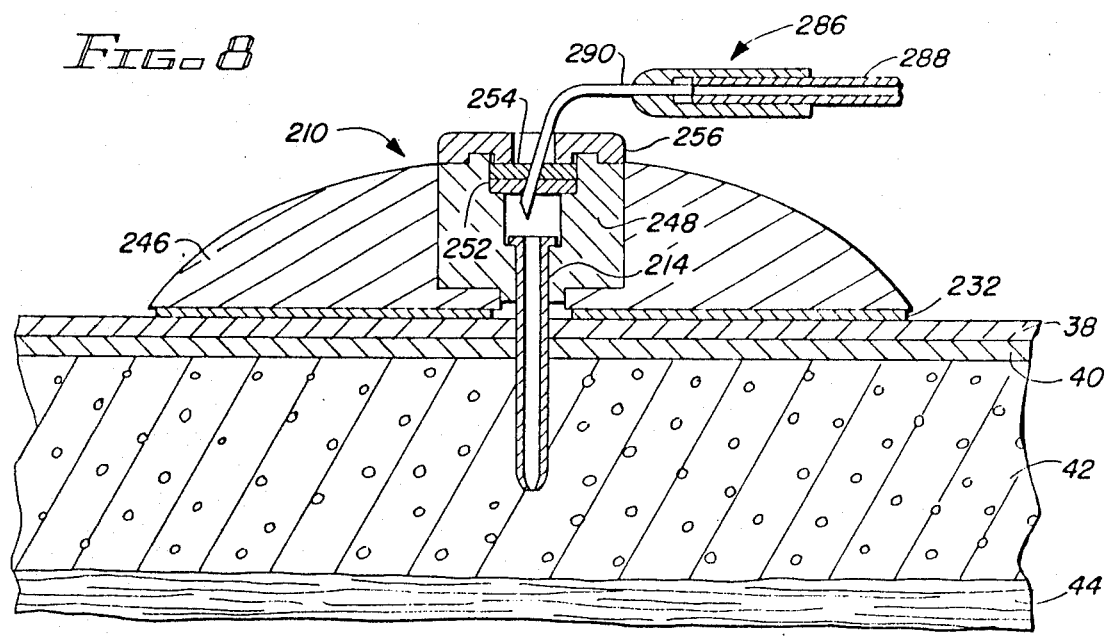
_FIG=8_
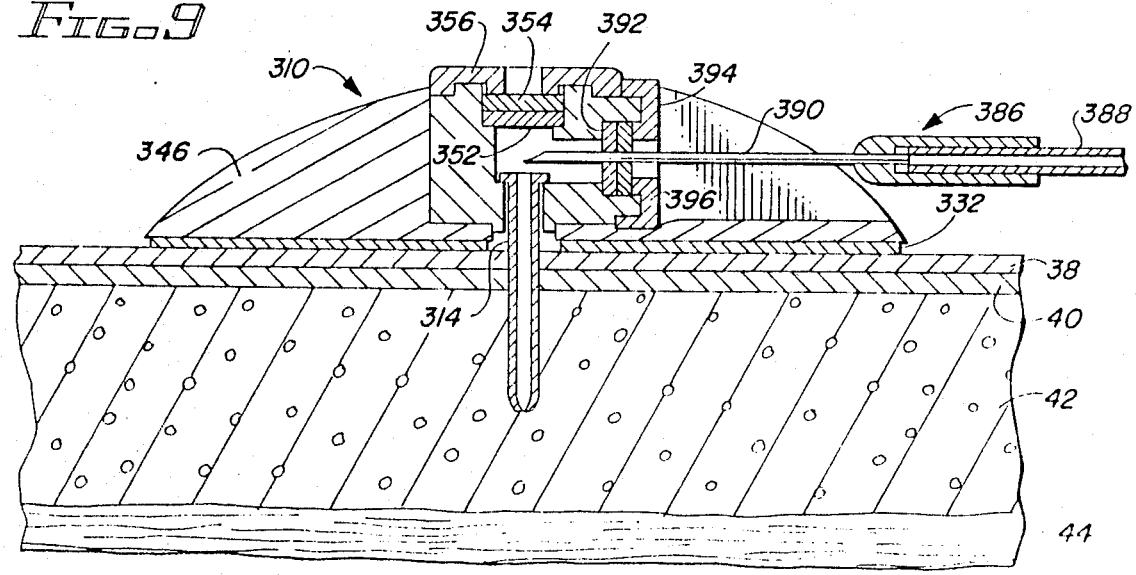
_FIG=9_

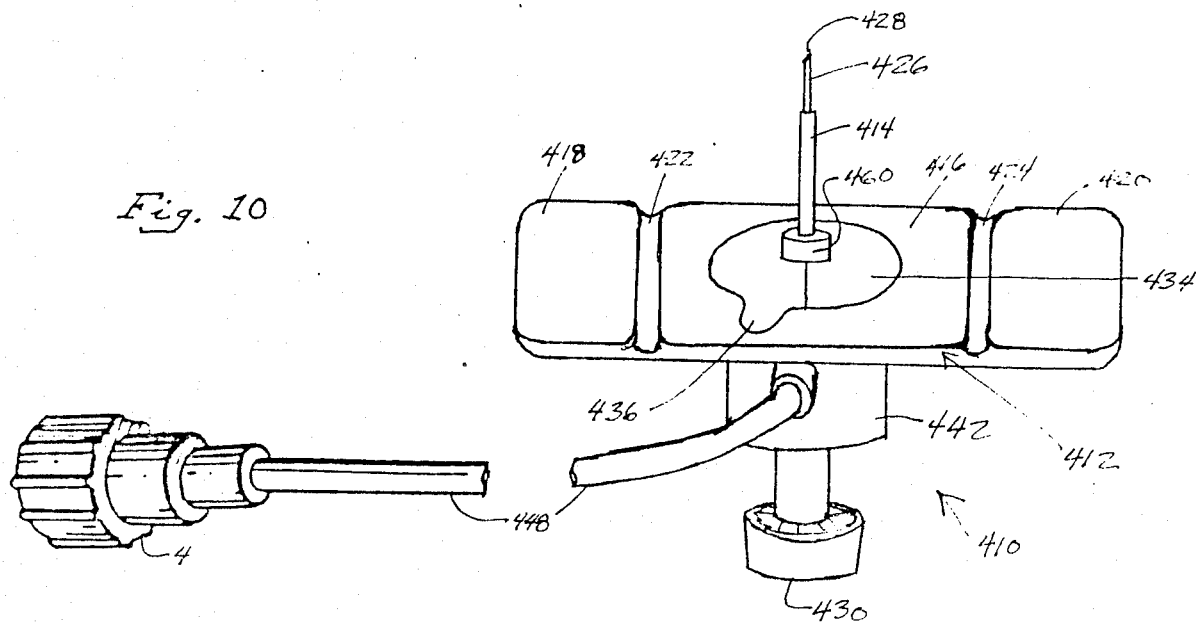
Fig. 10
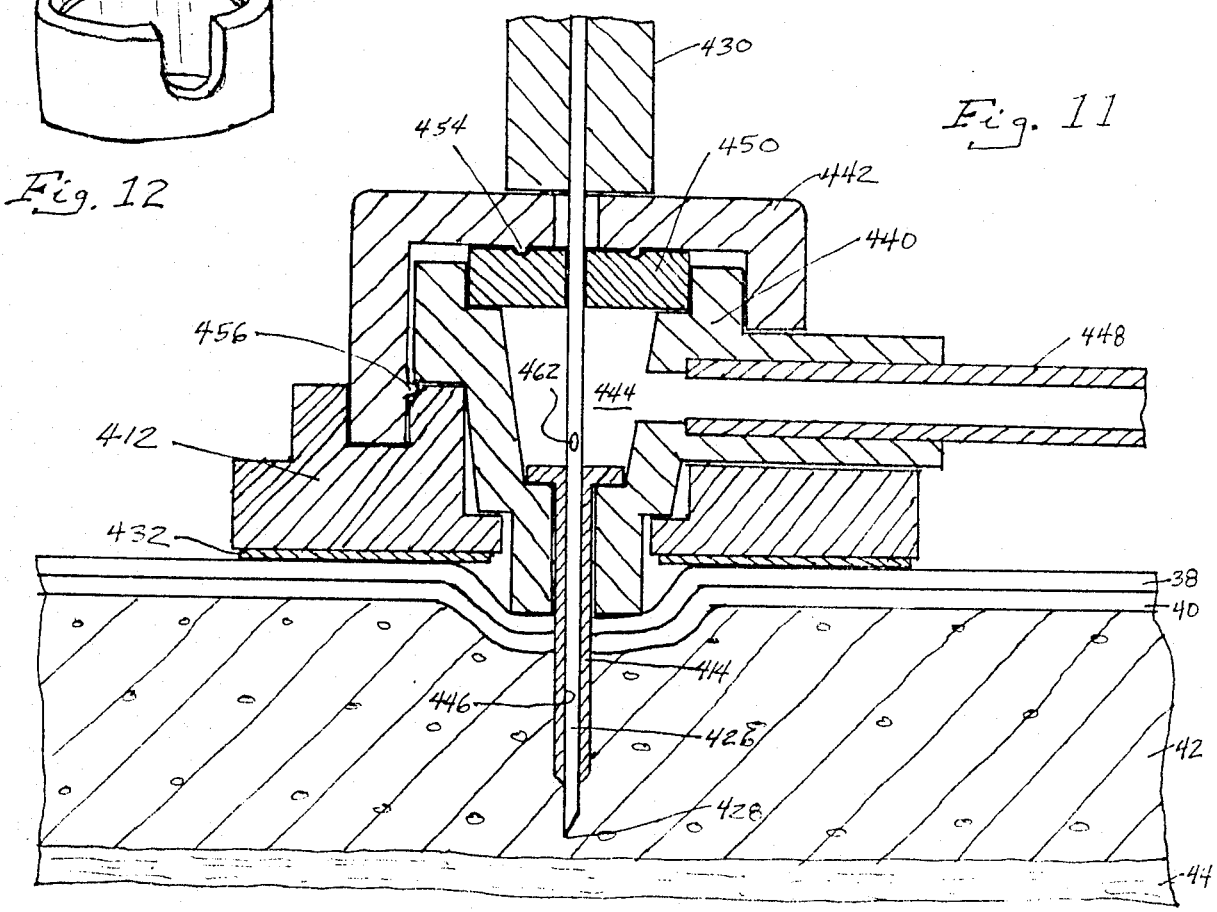
Fig. 12
Fig. 11

SOFT CANNULA SUBCUTANEOUS INJECTION SET

CROSS REFERENCE TO RELATED APPLICATION

This is a continuation-in-part of U.S. patent application Ser. No. 834,173, filed on Feb. 25, 1986, now abandoned.

BACKGROUND OF THE INVENTION

Field of the Invention

The present invention relates generally to injection devices for use with an external infusion system wherein a desired therapeutic fluid is subcutaneously delivered to a patient, and more particularly to a disposable subcutaneous injection set having a soft or flexible cannula which is inserted approximately normal to the skin to a desired subcutaneous injection level to deliver the therapeutic fluid with a minimum of discomfort and bother to the patient.

In general, whenever a therapeutic fluid is to be delivered subcutaneously to a patient form an external source, a passageway such as a hollow needle or other type of cannula or catheter device must first be inserted through the skin of the patient in order to provide a passageway or channel through which the fluid may pass from its source external to the patient to the desired subcutaneous location under the skin of the patient. Once this passageway has been installed, any suitable infusion device or system may be used in conjunction with an appropriate catheter connecting the external source of fluid with the passageway leading to the subcutaneous delivery point to deliver the fluid to the patient at an appropriate delivery rate.

Unfortunately, several problems attendant to infusing fluids into the patient as described above are usually encountered. In the first place, it is often uncomfortable, painful, and inconvenient to have a hollow needle or equivalent device piercing the patient's skin for prolonged periods of time. In addition, securing means must be used to keep the needle or equivalent device from moving from or within the injection site as the patient moves about. Such securing means are often quite bulky and bothersome to the patient, as well as being unsightly. There is also a continual risk of infection or inflammation at the skin puncture site. Moreover, the injection system must be primed prior to use. This involves removing all air or other gas from the connecting catheter and needle to thereby allow a known quantity of fluid to be safely dispensed therethrough.

A number of solutions attempting to address these problems have been offered. For example, it is known in the art to insert a soft cannula into the patient rather than a stiff, hard needle or equivalent device. Such a device is shown in U.S. Pat. No. 4,531,937, to Yates. A soft cannula is much more comfortable to the patient than such rigid devices. Insertion is accomplished using a removable stiff needle or stylet that passes tightly through a lumen of the soft cannula. A sharp tip of the needle extends from the end of the cannula when the needle is fully inserted therein. The sharp tip of the needle is inserted into the patient at the desired injection point, with the soft cannula following the needle and thereby being inserted therewith. Once both the needle and soft cannula are thusly inserted, the needle is withdrawn from the cannula, leaving the soft cannula in the patient and providing a more flexible and comfortable passageway through which fluid may be delivered to the patient at the desired subcutaneous site.

In Yates and other similar devices, removal of the needle from the soft cannula leaves an opening through which fluid may leak. While such an opening may be plugged by locating a self-sealing septum in the cannula, the problem of some degree of fluid leakage remains, particularly in those drug infusion systems having fluid delivery pressures much greater than those pressures encountered in gravity-feed injection systems.

Another proposed solution to the foregoing problems is the hard needle injection set, an example of which is shown in U.S. Pat. No. 4,235,234, to Whitney, et al. The injection set includes a locator pad having a sharp rigid needle protruding at a substantially right angle to the bottom surface of the locator pad. The bottom surface of the locator pad typically has a pressure sensitive adhesive applied thereto. Thus the needle is inserted into the skin of the patient while the locator pad is pressed against the skin at the same time in substantially the same motion, thereby securing the needle at the desired location. The needle has a right angle bend therein, positioned in the locator pad, to allow a delivery tube to be connected to the needle in a direction substantially parallel to the skin. This eliminates tubes or needles that might otherwise protrude perpendicularly from the skin, which protrusions can be not only a source of constant irritation and frustration to the patient, but also an easy target for accidental bumping by or entanglement with the patient's external environment.

Despite the beneficial features available with teachings of the art such as Whitney, et al, some problems common to injection sets still persist. For example with hollow needle injection systems a common problem is for the relatively small diameter lumen of the needle to become clogged or otherwise blocked or plugged, thereby preventing the free flow of fluid therethrough. This problem is aggravated in devices having a 90 degree bend placed in the needle, such as, for example, the Whitney, et al device. For this reason most injection sets, unlike the Whitney, et al and equivalent devices, shy away from 90 degree bends in the delivery channel. At most, such other devices utilize a "Y" shape, thereby minimizing the angle or bend in which a blockage could occur.

Another significant problem that occurs whenever a hollow needle or equivalent device (e.g., a solid needle having a channel or groove along one side) is employed to puncture the skin is that of "body coring." Body coring occurs when a piece of body tissue is cored out of the skin as the needle cuts therethrough. This piece of cored-out tissue remains in the lumen or channel of the needle and prevents fluid from flowing therethrough. In many injection systems, such as that illustrated in Whitney, et al, a body core can only be removed by removing the needle from the patient and flushing the system to force the cored tissue from the needle. Unfortunately, upon reinsertion there is a substantial risk that body coring may occur again. In other injection systems, such as those typified by Yates, body coring disadvantageously prevents the system from being primed in the proper manner.

In view of the above, it may be perceived that a substantial need exists for an injection set that combines the advantageous features of the devices discussed above, such as the use of a soft or flexible cannula and the use of a simple low-profile locator pad, but without the disadvantages encountered by such devices, namely the difficulties associated with priming and sealing the devices, and the problems associated with blocking or plugging of the devices.

SUMMARY OF THE INVENTION

The present invention teaches a disposable injection set that offers a soft or flexible cannula which is inserted essentially perpendicularly into the skin of a patient and held at its insertion location with a low profile holding pad or housing. The low profile holding pad is affixed to the skin of the patient, preferably with an antimicrobial pressure sensitive adhesive applied to a bottom surface thereof. The soft cannula protrudes from the bottom surface of the holding pad to a desired subcutaneous delivery level. An external source delivers fluid to the injection set via a catheter or tube which connects with the low profile holding pad at an angle substantially parallel to the skin of the patient, thereby minimizing the noticeable protrusion and the attendant nuisance or hindrance to the patient.

A small volume fluid chamber within the low profile holding pad or housing is utilized to connect the soft cannula, which is secured within the holding pad, with the delivery tube. This connection is accomplished in a way that eliminates any sharp bends or narrow openings particularly susceptible to clogging. A rigid insertion needle included with the injection set is initially inserted through a self-sealing septum wall contained in the housing, and this needle tightly fits within a lumen in the soft or flexible cannula. A sharp tip of the insertion needle extends beyond the end of the cannula when the insertion needle is fully inserted into the injection set. This sharp tip is used to puncture the skin of the patient, and thereafter the insertion needle provides the support for inserting the soft cannula subcutaneously into the patient. Once the soft cannula and insertion needle are inserted into the patient, and the bottom surface of the holding pad is pressed against and affixed to the skin of the patient, the insertion needle may be removed from the injection set, thereby leaving the soft cannula inserted into the patient. The self-sealing septum in the housing, through which the insertion needle is inserted, assures that fluid does not leak out of the housing when the insertion needle is withdrawn.

A notable feature of the present invention is the ease with which the soft or flexible cannula may be inserted and secured to the skin of the patient. Additionally, there need be no concern as to whether body cored tissue will plug or stop delivery of the fluid, or otherwise interfere with priming of the system, because priming occurs before insertion and therefore before any body coring could occur. Following insertion, any cored tissue will remain in the insertion needle, and the needle is removed, thereby carrying any cored tissue with it out of the device. The present invention also has the ability to allow the injection set to be primed prior to insertion of the soft cannula into the patient.

Since the holding pad includes a layer of pressure sensitive adhesive on its bottom surface, which adhesive in the preferred embodiment includes an anti-microbial substance to minimize the risk of infection or inflammation at the skin puncture point, only minimal preparation needs to be done to the patient's skin at the injection site prior to insertion of the insertion needle and application of the holding pad onto the skin. In the preferred embodiment, an additional adhesive patch is used to further hold the injection set to the skin surface, thereby preventing inadvertent movement of the injection set which could interfere with fluid delivery through the injection set.

Another feature of the preferred embodiment of the present invention is the provision of means for preventing the soft cannula from becoming kinked. Soft cannula injection sets are particularly vulnerable to kinking, which occurs mainly due to incomplete insertion of the soft cannula prior to removal of the insertion needle. Following removal of the insertion needle, the device is further pressed against the skin, causing the soft cannula to become kinked, thereby blocking the flow of fluid. With the present invention, this occurrence is effectively prevented.

The preferred embodiment of the present invention also utilizes an improved holding pad configuration. Placement of the injection set on the skin in an area in which the skin will be flexed has in the past caused the cannula to be partially removed from the subcutaneous tissue. With a soft cannula, this problem is exacerbated since the soft cannula will bend, possibly blocking the flow of medication therethrough. By using a holding pad which has some degree of movement therein while maintaining the soft cannula completely inserted into the subcutaneous tissue. The preferred embodiment allows greater reliability than ordinarily found in a soft cannula injection set. Finally, another feature of the present invention is the free flow subcutaneous delivery channel that is provided once the injection set has been put in place, since this delivery channel has the capacity to deliver larger volumes of fluid than have heretofore been possible. These and other advantages of the present invention are all obtained without incurring any relative disadvantage.

BRIEF DESCRIPTION OF THE DRAWINGS

These and other advantages of the present invention are best understood with reference to the drawings, in which:

FIG. 4 is a sectional view of the injection set of FIG. 1 when inserted into the skin of the patient and after the insertion needle has been withdrawn;

FIG. 5A is an enlarged view of a multi-layer septum having a needle inserted therethrough;

FIG. 5B is an enlarged view of a multi-layer septum as in FIG. 5A with the needle removed therefrom;

FIG. 6 is a perspective view of the injection set of FIG. 1 showing how the protective covering is removed from the pressure-sensitive adhesive on the bottom side of the holding pad, a needle guard installed over the needle and cannula, and an alternate shape for the handle of the needle;

FIG. 7A is an enlarged view of an alternate embodiment using a silicone gel system septum having a needle inserted therethrough;

FIG. 7B is an enlarged view of the silicone gel system septum as in FIG. 7A with the needle removed therefrom;

FIG. 8 is a sectional view of an alternate embodiment top port button injection set;

FIG. 9 is a sectional view of an alternate embodiment side port button injection set;

FIG. 10 is a perspective view of an injection set which is the preferred embodiment of the present invention, shown as it would appear prior to being applied to a patient;

FIG. 11 is a sectional view of the injection set of FIG. 10 when inserted into the skin of the patient and before the insertion needle has been withdrawn;

FIG. 12 is a perspective view of the retaining cap of the injection set shown in FIGS. 10 and 11;

DETAILED DESCRIPTION OF THE PREFERRED EMBODIMENT

Figure 1:
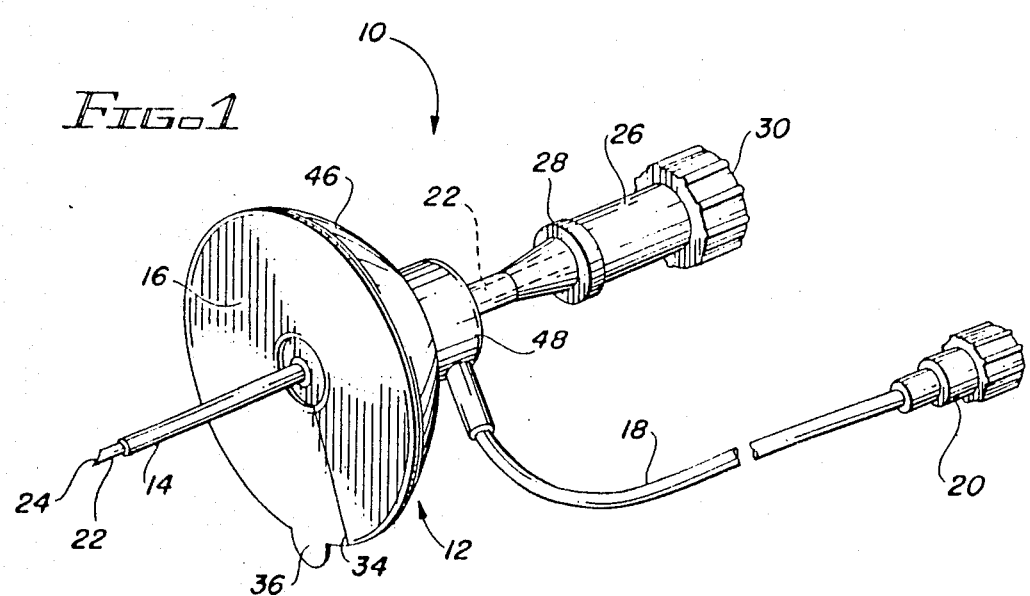
FIG. 1 is a perspective view of an injection set which is the first embodiment of the present invention, shown as it would appear prior to being applied to a patient.

Referring to FIG. 1, a perspective view of a first embodiment of the injection set 10 of the present invention prior to insertion into a patient is shown. The injection set 10 includes a holding pad 12 having a soft cannula 14 protruding from a bottom surface 16 thereof at an angle of between 15 and 90 degrees, preferably approximately perpendicularly. A delivery tube 18 is connected at one end to the holding pad 12 at an angle substantially parallel to the bottom surface 16. The other end of the delivery tube 18 is fitted with a conventional female luer connector 20 which may be readily connected or coupled to a suitable source of fluid (not shown).

Prior to insertion into the patient, the soft cannula 14 has a hard insertion needle 22 inserted therein. The insertion needle 22 has a sharp tip 24 which extends beyond the end of the soft cannula 14 when the insertion needle 22 is fully inserted. The insertion needle 22 further includes a handle 26 or other means for allowing the insertion needle 22 to be firmly gripped by the fingers of a person who is inserting the injection set 10. The handle 26 shown in FIG. 1 includes a lower rim 28 and an end cap 30 to facilitate gripping the handle 26. The lower rim 28 may be gripped between two fingers while a thumb may be placed against the top of the end cap 30, thereby providing a means for applying both pushing and pulling forces on the insertion needle 22. Other types of handles could, of course, be used to facilitate gripping of the insertion needle 22. For example, an alternative type of handle 80 is shown in FIG. 6.

Figure 2:
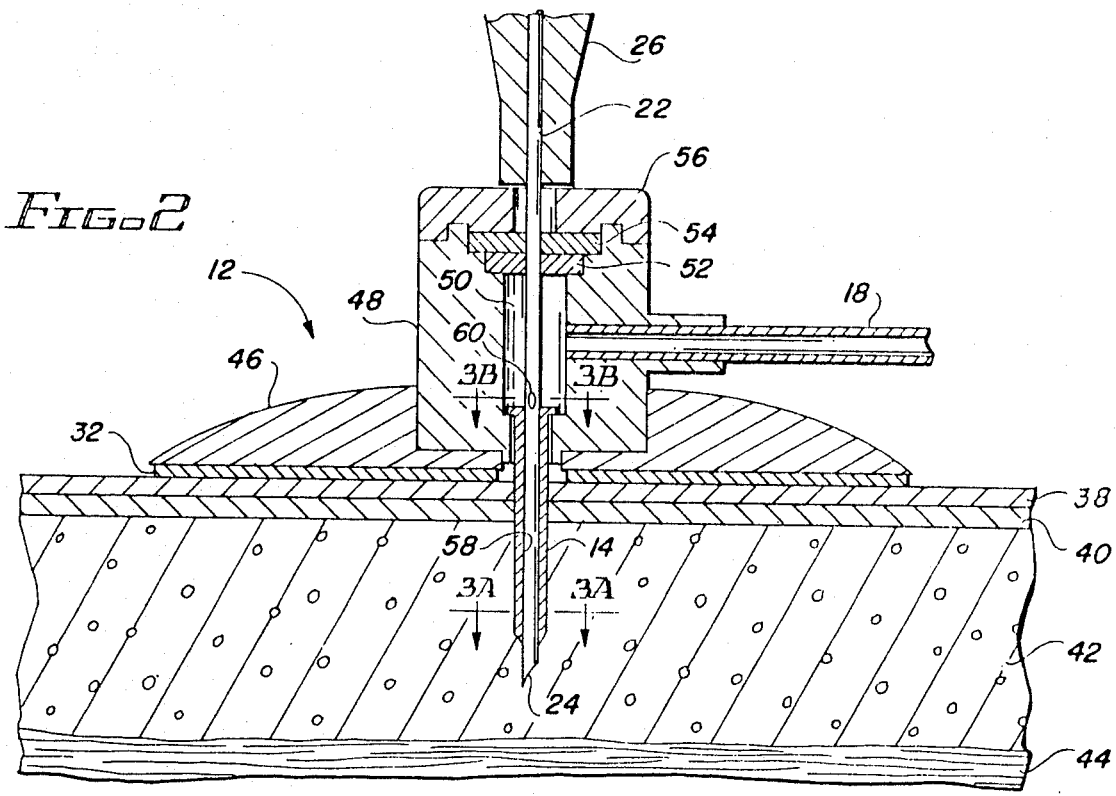
FIG. 2 is a sectional view of the injection set of FIG. 1 when inserted into the skin of the patient and before the insertion needle has been withdrawn.

The bottom surface 16 of the holding pad 12 is coated with a layer of pressure-sensitive adhesive 32 (best shown in FIGS. 2 or 4). This layer 32 is covered with a protective paper backing 34 having a pull tab 36. The manner in which the protective paper backing 34 is removed from the bottom surface 16 will be explained more fully below in conjunction with FIG. 6.

Referring next to FIG. 2, a sectional view of the injection set 10 taken generally through the center thereof is shown after the injection set 10 has been inserted into the skin of a patient, but prior to removable of the insertion needle 22. The skin of the patient is comprised of several layers of body tissue as shown in FIG. 2. An epidermis layer 38 comprises the outer layer of the skin. Underneath the epidermis layer 38 and the dermis layer 40 is a subcutaneous fat layer 42. Muscle tissue 44 generally lies beneath the subcutaneous fat layer 42. In accordance with the teachings of the present invention, the soft cannula 14 is inserted through the layers of skin 38 and 40 and into the subcutaneous fat layer 42. It is desirable that the cannula 14 not protrude into the muscle tissue 44, inasmuch as the muscle tissue 44 absorbs insulin (and other medications) at different rates than does the subcutaneous fat layer 42.

The holding pad 12 includes a domed base portion 46 and a central hub portion 48. A fluid chamber 50 is centrally located within the central hub portion 48. Both the soft cannula 14 and the delivery tube 18 are in fluid communcation with the fluid chamber 50.

For the embodiment shown in FIG. 2, a first septum layer 52 and a second septum layer 54 cover or enclose the top of the fluid chamber 50. A cap 56, suitably bonded to the top portion of the central hub 48, securely holds the septum layers 52, 54 in their desired location, as explained more fully below. The insertion needle 22 is inserted through the septum layers 52, 54 and through a lumen 58 of the soft cannula 14. Fluid communication means are provided within the insertion needle 22 to allow fluid, and hence air or other gases, to readily flow between and aperture or opening 60 of the insertion needle 22 (which is positioned within the chamber 50 when the insertion needle 22 is fully inserted into the injection set 10) and the insertion needle tip 24. As seen in the sectional views of FIGS. 3A, 3B, and 3C, this fluid communication means may be realized with at least one of two different embodiments.

Figure 3A:
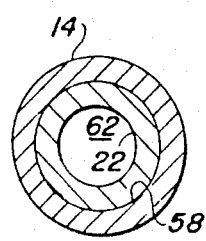
FIG. 3A is a sectional view taken along the line 3A—3A of FIG. 2 for a hollow insertion needle embodiment of the invention.
Figure 3B:
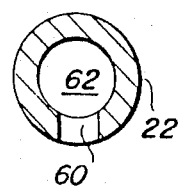
FIG. 3B is a sectional view taken along the ling 3B—3B of FIG. 2 to show the aperture in the hollow insertion needle embodiment of the invention.

In the embodiment shown in FIGS. 3A and 3B, the insertion needle 22 is hollow having a bore 62 through the center thereof. In an alternate embodiment, shown in FIG. 3C, an insertion needle 122 is shown which is solid and has a groove or channel 64 along one side thereof. In either embodiment, a tight fit within the lumen 58 of the soft cannula 14 is achieved.

Note also that the end of the soft cannula 14 is slightly tapered to enchance the insertion of the soft cannula 14. The needle bore 62, in conjunction with the hole or aperture 60 in the insertion needle 22 positioned within the fluid chamber 50 (for the embodiment of FIGS. 3A and 3B), or the groove or channel 64 of the insertion needle 122 which would terminate within the fluid chamber 50 (for the embodiment of FIG. 3C), provides the fluid communication means between the fluid chamber 50 and the needle tip 24.

The fluid communication means provided by the bore 62 (or the groove 64 in the alternate embodiment) allows the injection set 10 to be easily primed prior to insertion into the patient. All that need be done to prime the injection set 10 is to point the tip 24 of the insertion needle 22 in an upwards direction at the same time that the fluid to be injected is inserted into the end of the delivery tube 18 having the connector 20 thereon. As the fluid passes through the delivery tube 18 into the fluid chamber 50, all of the air that was previously inside the delivery tube 18 and the fluid chamber 50 will escape through the bore 62 (or groove 64) of the needle 22 (122).

Note that since the fluid chamber 50 is very small, typically less than one-half unit in volume, the removal of all air in this operation will likely take place irrespective of the positioning of the tip 24; however, this positioning is recommended. When all of the air has thusly been removed, and the system is primed, the fluid itself will begin to exit from the tip 24 of the insertion needle 22; thereby signaling to the person using the device that the desired priming has been accomplished.

It is perferable that the material from which the delivery tube 18 and the central hub 48 of the holding pad 12 are made is transparent, to thereby provide means for visually determining whether all of the air bubbles have been removed from the delivery tube 18 and the fluid chamber 50.

With all of the air thusly removed from the system, the injection set 10 may then be inserted into the patient in the same manner as any needle would be inserted into a patient by a nurse, or doctor, or by the patient himself or herself. As stated above, the amount of fluid contained within the tube 18 and fluid chamber 50 of the primed injection set is not large, typically less than one-half unit. In any event, it is a known amount that the patient and/or doctor can use, as needed, to determine the amount of fluid that has been delivered to the patient over a period of time.

Referring next to FIG. 4, a sectional view of the injection set 10 is shown as it appears when attached to a patient after the insertion needle 22 (shown in Figure 2) has been removed therefrom. FIG. 4 also shows a desired fluid 66 (represented as small dots), delivered from an infusion pump (not shown) or similar delivery system, that flows through the delivery tube 18, into the fluid chamber 50, and through the lumen 58 of the soft cannula 14 so as to be dispersed at the desired delivery point within the subcutaneous fat layer 42 of the patient. The inner diameter of the lumen 14, typically approximately 24 gauge and the smallest opening associated with the delivery system, allows appropriate amounts of fluid 66 to be delivered under control of the infusion pump (not shown) without excessive flow restrictions. Since this delivery channel has the capacity to deliver larger volumes of fluid than have heretofore been possible, what in essence is virtually a free flow subcutaneous delivery channel is provided once the injection set has been put in place.

The injection set 10 as shown and described herein has two septum layers 52, 54. However, the teachings of the present invention apply to devices having one or more septum layers, and the discussion of the exemplary embodiment having two layers should not be allowed to obfuscate this point. In fact, the additional layers may be used to provide even greater assurance of an effective seal. As shown in FIG. 4, the septum layers 52, 54 have sealed once the insertion needle 22 (FIG. 2) has been withdrawn therefrom, thereby preventing the fluid 66 from leaking out of the chamber 50 through an aperture 68 in the end cap 56.

Because the fluid 66 is typically delivered from the infusion pump (not shown) under a substantial pressure (at least relative to the minimal pressures that are typically associated with gravity-flow fluid delivery systems), it is critically important that the septum layers 52, 54 provide an effective seal for preventing the fluid 66 from escaping or leaking out of the fluid chamber 50. In order to ensure a tight seal with the septum layers 52, 54, these septum layers 52, 54 are prestressed with compressive forces as illustrated in the partial sectional views of FIGS. 5A and 5B.

Referring first to FIG. 5A, a partial sectional view of the fluid chamber 50 and septum layers 52, 54 having the insertion needle 22 inserted therethrough is shown. Insertion of the insertion needle 22 through the septum layers 52, 54 necessarily causes the cutting or making of openings 72, 74 through the septum layers 52, 54, respectively. In a conventional septum, the resilient nature of the septum material is relied upon to close the openings 72, 74 once the piercing insertion needle 22 has been removed therefrom. In order to ensure that this sealing or closing occurs, this embodiment of the present invention places compressive forces on the septum layers 52, 54 in at least two directions.

For example, as represented by the horizontal arrows 76 the septum layers 52, 54 are compressed radially inwardly towards the center thereof. Similarly, as represented by the downward pointing arrows 78, a shear compressive force is applied to the upper side of the septum layers 54 and 52. In the preferred embodiment, adjacent septum layers such as 52, 54 are made of different materials. Also, the effective forces on each of the septum layers 52, 54 will necessarily differ. The net effect of typical compressive forces applied to the septum layers 52, 54 is illustrated in FIG. 5B wherein it is seen that any residual openings 72, 74 through the septum layers 52, 54, respectively, will not align, thereby assuring that an effective seal is realized.

The horizontal compressive forces 76 are realized simply by sizing the septum layers 52, 54 to be slightly larger than the openings into which they are inserted. The vertical compressive forces 78 are realized by applying the end cap 56 over the septum layers 52, 54 as shown in FIGS. 2 and 4 so as to constantly assert a downward pressure or force. In the embodiment shown, the septum layer 52 may be realized from butyl, a substance known to be compatible with insulin and other fluids that would likely be injected through the injection set of the present invention The septum layer 54, on the other hand, may be realzed with silicon. Because silicon and butyl have somewhat different properties, especially in response to the compressive forces that are applied, the use of differnt materials in these respective septum layers further assures that an appropriate seal is realized. As stated above, while two septum layers are shown in the figures, one, two, or more septum layers subjected to appropriate compressive forces could be used as described.

The method of making an injection set 10 according to the present invention will now be described. First, the domed base 46 and the central hub 48 of the holding pad 12 are molded using appropriate known molding techniques and tools. While the sectional views presented herein suggest that the central hub 48 is a separate part from the domed base 46, this is not required. In practice, it may be easier to mold the central hub 48 and domed base 46 as in integral part. In the preferred embodiment, the materials from which the domed base 46 and central hub 48 are made are a rigid material such as rigid PVC for the central hub 48, and a flexible material such as flexible PVC for the domed base 46. These materials will typically cure so as to be clear or transparent, thereby allowing visual indication that all of the air has been removed from the system when the system is primed.

The molding process would include means for leaving an aperture or channel in the bottom of the central hub 48 and through the center of the dome base 46 through which the soft cannula 14 may be attached. A second aperture through which the delivery tube 18 may be attached is located in the side of the central hub 48. The soft cannula 14 may be made of a teflon tube of an appropriate diameter and thickness. Such a soft cannula 14 will typically have a hardness of between 35 and 75 on the Shore D scale, with the preferred hardness being approximately 55 on the Shore D scale. The soft cannula 14 is inserted and swedged or heat sealed to the hub 48 so as to be in fluid communication with the fluid chamber 50. Similarly, the delivery tube 18 may be sealably bonded with solvent to the hub 48 so as to be in fluid communication with the chamber 50.

An alternative material which may be used for the soft cannula 14 is hydrogel material, best known as the primary material in soft contact lenses. Hydrogel material is ideal since it is rigid when dry, making a hydrogel cannula easily insertable. Inside body tissue, a hydrogel cannula would lose its rigidity, and become soft and supple. A hydrogel cannula would be more comfortable. Additionally, insulin absorption may be better controlled with a hydrogel cannula since the entire length of the hydrgoel cannula could act as a depot site for insulin absorption. The hydrogel cannula may also be fastened to the hub 48 by solvent, or by being swedged or heat sealed.

The septum layers 52, 54 may be sealably bonded to the upper portion of the hub 48 so as to cover or seal the chamber 50, although this bonding operation is optional. As indicated previously, these layers are typically sized somewhat larger than the openings into which they are inserted, thereby ensuring that appropriate compressive forces are radially applied therto. Next, the insertion needle 22 is inserted through the septum layers 52, 54 and through the lumen 58 of the cannula 14.

Once the insertion needle 22 is in place, the cap 56 is placed over the septum layers 52, 54 thereby applying a shearing compressive force thereto and sealing the chamber 50. This cap 56 may be secured in place either by a snap fit, a sonic seal, a solvent bond, or a cold roll process, thereby ensuring that sufficient compressive forces are applied thereto. Alternatively, the insertion needle 22 may be inserted after the installation of the cap 56.

Finally, the pressure sensitive adhesive layer 32 may be applied to the bottom surface 16 of the base portion 46. Pressure-sensitive adhesive may be applied to both sides of a suitable base film or substrate (in a manner similar to double-sided adhesive tape) which is precut to cover the entire bottom surface 16. One side of the adhesive layer 32 is then pressed into position on the bottom surface 16 of the base portion 46. The protective covering or backing 34 is installed on the other side of the adhesive layer 32 to protect the exposed side of the adhesive until such time as the injection set 10 is ready for use.

As indicated previously, the pressure-sensitive adhesive 12 preferably includes an appropriate anti-microbial substance which helps prevent infection and inflammation which may occur at the puncture site. This anti-microbial substance may be coated onto the side of the adhesive layer 32 away from the base portion 46 by suspending a determined percentage of anti-microbial substance in an isopropyl alcohol solution. This solution may then be coated into the adhesive in the adhesive layer 32 on the side away from the base portion 46, which side will be coming into contact with the edpidermis upon installation of the injection set 10. The alcohol may then be driven off by a heat cure normally used during the adhesive coating process.

Referring next to FIG. 6, the injection set is shown with the protective backing 34 partially pulled therefrom. The backing 34 may be cut radially so that when the pull tab 36 is pulled away from the pressure-sensitive adhesive, the backing 34 peels off of the bottom surface 16 in a spiral motion which does not disturb the protruding soft cannula 14 or the insertion needle 22. This helps ensure that the protruding cannula 14 and the insertion needle 22 are not accidentally bumped or otherwise improperly touched prior to insertion. A needle guard 82 made of clear PVC and installed over the soft cannula 14 and the insertion needle 22 is also helpful in this respect. FIG. 6 also shows an alternative embodiment for a handle 80 on the insertion needle 22, which handle 80 is essentially a finger tab which is securely affixed to the end of the insertion needle 22.

An alternative arrangement to the septum layers 52, 54 is shown in FIGS. 7A and 7B. A three layer septum arrangement is illustrated between the central hub 48 and the cap 56. A layer of silicone gel such as Dow Corning Q7-2218 silicone gel is sandwiched between a first layer of vulcanized silicone 152 and a second layer of vulcanized silicone 154 to produce a laminated segment. The laminated segment would preferably be constructed prior to installation between the central hub 48 and the cap 56. The silicone gel 84 is viscous enough to remain sandwiched between the layers of vulcanized silicone 152, 154. The three layer segment of septum material may be cut to size by use of a laser or other means.

In FIG. 7A, the insertion needle 22 is shown extending through the layers of vulcanized silicone 152, 154 and the silicone gel 84 contained therebetween. Following removal of the insertion needle 22, residual openings 172, 174 will exist in the layers of vulcanized silicone 152, 154, as shown in FIG. 7B. The silicone gel 84 is too viscous to seep through the residual openings 172, 174, and will thereby assure a complete and total seal of the residual openings 172, 174.

Two further alternate embodiments of the present invention are illustrated in FIGS. 8 and 9. These embodiments are for use with standard infusion sets, with the embodiment shown in FIG. 8 being used with a standard infusion set having a needle containing a substantial bend therein, and the embodiment shown in FIG. 9 being used with a standard infusion set having a straight needle.

Referring first to FIG. 8, a soft cannula button diffuser 210 is illustrated which has a central hub 248 mounted in a domed base 246. The central hub 248 is substantially similar to the central hub 48 of the preferred embodiment (FIGS. 2 and 4), but the central hub 248 lacks an opening therein for a delivery tube. Two septum layers 252, 254 are mounted in the central hub 248, and they are secured by a cap 256 in a manner substantially similar to the primary embodiment of the present invention. A soft cannula 214 is secured to the central hub 248and extends through the domed base 246, as in the preferred embodiment. A layer of pressure-sensitive adhesive 232 is used to secure the soft cannula button infuser 10 to the epidermis 38.

The installation of the soft cannula button infuser 210 is identical to the installation of the preferred embodiment of the present invention, as shown in FIG. 2. An insertion needle 22 would be inserted through the septum layers 252, 254 and through the lumen of the soft cannula 214. The soft cannula button infuser 210 could then be installed into the skin of the user, and the insertion needle 22 withdrawn as described in conjunction with the preferred embodiment as shown in FIGS. 2 and 4.

A standard infusion set 286 fed by a delivery tube 288 and having a 27 gauge angled needle 290 is used to supply fluid to the soft cannula button infuser 210. When the angled needle 290 is inserted through the septum layers 252, 254, it may be seen that the delivery tube 288 will extend from the soft cannula button infuser 210 in a position substantially parallel to the skin.

The soft cannula button infuser 210 shown in FIG. 8 possesses a substantial advantage over the preferred embodiment to the present invention shown in FIGS. 2 and 4 in that the soft cannula button infuser 210 facilitates a quick disconnect from the source of fluid by merely removing the angled needle 290 from the device, whereupon the septum layers 252, 254 will immediately seal. Such a quick disconnect affords the patient the flexibility of taking a shower, bath, or swim without necessitating the removal of the injection set and reintroduction of a new injection set following the completion of the activity.

A second alternate embodiment having the same advantages of the embodiment illustrated in FIG. 8 is shown in FIG. 9. A soft cannula side port button infuser 310 has a central hub 348 mounted in a domed base 356, which domed base 346 is attached to the epidermis 38 with the use of a layer of pressure-sensitive adhesive 332. The central hub 348 has a soft cannula 314 connected thereto in a manner substantially similar to that described above in conjunction with FIG. 8, as well as the primary embodiment of the present invention as shown in FIGS. 2 and 4. Two septum layers 352, 354 are mouned in the central hub 348 and held in place by a cap 356, as discussed above. The introduction of the soft cannula side port button infuser 310 to the patient is exactly as discussed above in conjunction with FIG. 8.

The soft cannula sided port button infuser 310 of FIG. 9 differs from the device shown in FIG. 8 in that it has a side port for admitting the fluid to the central hub 248. Two additional septum layers 392, 394 are mounted in the central hub 348 at a location in a side of the central hub 348 which is open. The septum layers 392, 394 are secured in the location in the side of the central hub 348 by an additional cap 396.

A standard infusion set 386 fed by a delivery tube 388 and having a straight 27 gauge needle may be used to supply the soft cannula side port button infuser 310. The straight needle 390 is inserted through the septum layers 392, 394, so that the needle 390 is in communication with the interior of the central hub 348. It should be noted that the domed base 346 does not extend completely around the central hub 348, with an opening being left in the domed base 346 around the cap 394. It may be appreciated that the soft cannula side port button infuser 310 illustrated in FIG. 9 has the lowest profile of any of the devices discussed in this specification to this point, since the infusion set 386 is connected to the device at the side thereof. Therefore, it may be seen that the soft cannula side port button infuser 310 illustrated in FIG. 9 possesses the same advantage of the device illustrated in FIG. 8, namely that it facilitates convenient disconnection and reconnection of the device to a source of fluid.

Figure 14:
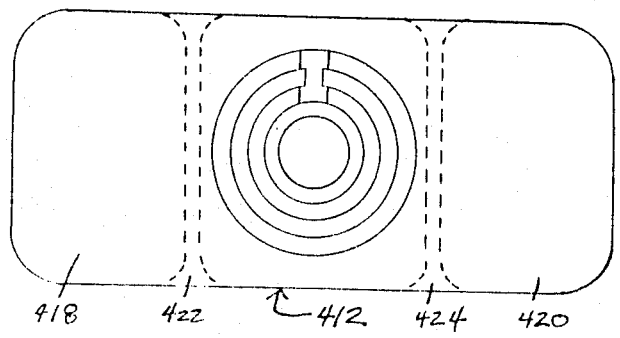
FIG. 14 is a plan view from the top of the holding pad of the injection set shown in FIGS. 10 and 11.

Referring now to FIG. 10, a perspective view of an injection set 410 which is the preferred embodiment of the present invention is shown. The injection set 410 includes a holding pad 412, and, like the previous embodiments discussed above, has a soft cannula 414 protruding from the bottom thereof essentially perpendicularly to the holding pad 412. The holding pad 412 is essentially rectangular in outline, and the bottom side of the holding pad 412 is shown in FIG. 10 (the top side of the holding pad is shown in FIG. 14). The holding pad 412 has a central portion 416 from which the soft cannula 414 protrudes, and two wing portions 418, 420, extending from opposite sides of the central portion 416. The two wing portions 418, 420 are connected to the central portion 416 by two areas of reduced thickness 422, 424, respectively. It will therefore be appreciated that the two areas of reduced thickness 422, 424 act as hinges to allow the two wing portions 418, 420 to move with respect to the central portion 416, thereby enabling the holding pad 412 to fit to the contour rather well. The holding pad 412 may be molded out of a flexible material such as flexible PVC.

Prior to insertion into the patient, the soft cannula 414 has a hard insertion needle 426 with a sharp tip 428 inserted therein, the insertion needle 426 extending beyond the end of the soft cannula 414 when fully inserted. The insertion needle 426 also includes a handle 430 to allow the insertion needle 426 to be firmly gripped by the fingers of a person who is inserting the injection set 410.

The bottom of the central portion 416 of the holding pad 412 is coated with a circular layer of pressure-sensitive adhesive 432 which is covered with a protective paper backing 434 having a pull tab 436. The pressure-sensitive adhesive 432 is the same as the adhesive layer 32 discussed above in conjunction with FIGS. 1-6, and again preferably includes an appropriate anti-microbial substance to help prevent infection and inflammation which may occur at the puncture site. The backing 434 is again preferably cut radially so that when the pull tab 436 is pulled away from the pressure-sensitive adhesive 432, the backing 434 peels off in a spiral motion which does not disturb the protruding soft cannula 414 or the insertion needle 426. A needle guard (not shown) made of clear PVC would also be used to cover the soft cannula 414 and the insertion needle 426 prior to use.

Referring next to FIG. 11, a sectional view of the injection set 410 taken generally through the center thereof is shown with the injection set 410 inserted into the skin of a patient prior to removable of the insertion needle 426. The holding pad 412 has mounted thereon a catheter hub 440 and a retaining cap 442. A fluid chamber 444 is centrally located within the catheter hub 440, with a lumen 446 extending through the soft cannula 414 being in fluid communication with the fluid chamber 444. One end of a delivery tube 448 is connected to the catheter hub 440 at an angle substantially parallel to the bottom of the holding pad 412 (and hence the skin of the user), and the delivery tube 448 is in fluid communication with the fluid chamber 444. The other end of the delivery tube 448 is connected to a female luer connector 449, which may be connected to a source of fluid (not shown).

The catheter hub 440 is preferably molded of clear rigid PVC, and has an aperture or channel in the bottom thereof through which the soft cannula 414 is attached. The soft cannula 414 is preferably made of teflon tube typically having a hardness of between 35 and 75 on the Shore D scale, with the preferred hardness being approximately 55 on the Shore D scale. Again, hydrogel material is an alternative material which may be used for the soft cannula 414. The soft cannula 414 is inserted and either bonded, or swedged or heat sealed (typically by sonic welding), to the catheter hub 440 so that the lumen 446 of the soft cannula 414 is in fluid communication with the fluid chamber 444. The end of the soft cannula 414 may also be slightly tapered to enhance the insertion of the soft cannula 414.

A second aperture through which the delivery tube 448 may be attached is located in the side of the catheter hub 440. The delivery tube 448 may be sealably bonded with solvent to the catheter hub 440 so as to be in fluid communication with the chamber 444.

Figure 13:
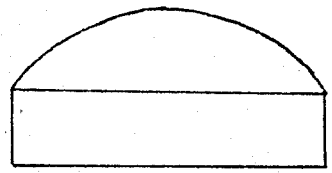
FIG. 13 is a side view of the single layer septum of the injection set shown in FIGS. 10 and 11.

The catheter hub 440 is molded to receive a circular cross-section septum 450, shown compressed in FIG. 11 and in an uncompressed state in FIG. 13. The septum 450 is made of a sealing elastomeric material such as medical grade silicone rubber, or silastic, and has a rounded top which will be compressed by the installation of the retaining cap 442. The septum 450 seals the top of the chamber 444 upon compression.

While the septum 450 of the preferred embodiment has only one layer, two or more septum layers could be used as described herein. Only one layer is necesary for most applications. While the septum 450 may be sealably bonded to the catheter hub 442 to seal the chamber 444, this bonding operation is optional and is not necessary for most applications.

The retaining cap 442 is placed over the catheter hub 440, thereby applying a compressive force to the septum 450 and sealing the chamber 444. The retaining cap 442 has an aperture in the top thereof to slidably admit the insertion needle 426. On the inside of the top of the retaining cap 442, spaced away and around the aperture, is a raised circular sealing ring 454, which presses into the top of the septum 450 to enhance the sealing characteristics of the device.

The retaining cap 442 is secured in place on the catheter hub in the preferred embodiment by a snap fit. A raised snap ring 456 extends around the lower inside edge of the retaining cap 442, as shown best in FIG. 12. In addition, a notch in the side of the retaining cap 442 fits over the portion of the catheter hub to which the delivery tube 448 is attached. The raised snap ring 456 snaps around the catheter hub 440 when the retaining cap 442 is placed thereon and compresses the septum 450. Note that the retaining cap may also be fastened to the catheter hub 440 with a sonic seal, a solvent bond, or a cold roll process.

The catheter hub 440 and the retaining cap may then be assembled to the holding pad 412, which has an aperture in the center of the central portion 416 thereof, and ridges to receive the retaining cap 442, as shown best in FIG. 14. The retaining cap 442 may be solvent bonded to the holding pad 412, or attached by other methods as described above.

A critical feature of the preferred embodiment of the present invention which is shown best in FIGS. 10 and 11 is that a cylindrial segment 460 of the catheter hub 440 extends through the aperture in the holding pad 412, and protrudes on the bottom side of the holding pad 412. The reason for this cylindrical segment 460 protruding from the holding pad 412, and the critical nature of the design, will become apparent below in conjunction with the discussion of FIG. 16.

At any point in this operation the insertion needle 426 may be inserted through the septum 460 and through the lumen 446 of the cannula 414. Again, fluid communication means are provided within the insertion needle 426 to allow fluid, and hence air or other gases, to readily flow between an aperture or opening 462 of the insertion needle 426 (which is positioned within the chamber 444 when the insertion needle 426 is fully inserted into the injection set 410) and the insertion needle tip 428 through a needle bore (not shown in FIG. 11) extending between the aperture 462 and the tip 428 of the insertion needle 426. This fluid communication means is the embodiment illustrated in FIGS. 3A and 3B, but fluid communication may also be accomplished by using the groove discussed in conjunction with FIG. 3C; both of these embodiments have been discussed fully above.

Figure 3C:
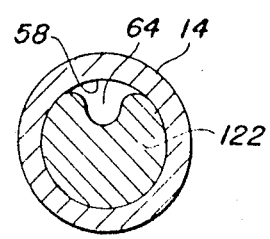
FIG. 3C is an analogous view to the view taken along the line 3A—3A and shown in FIG. 3A, but for a grooved insertion needle embodiment of the invention.

The injection set 410 is primed prior to insertion into the patient by pointing the tip 428 of the insertion needle 426 in an upwards direction at the same time that the fluid to be injected is inserted into the end of the delivery tube 448 having the connector 449 thereon. As the fluid passes through the delivery tube 448 into the fluid chamber 444, all of the air that was previously inside the delivery tube 448 and the fluid chamber 444 will escape through the aperture 462 and the bore within the insertion needle 426 (or the groove if the embodiment of FIG. 3C is utilized). Note that since the fluid chamber 444 is very small, less than one-half unit in volume, the removal of all air in this operation will likely take place irrespective of the positioning of the needle tip 428; however, this positioning is recommended. In addition, the amount of fluid needed to prime the injection set 410 is a known amount that the patient and/or doctor can use, as needed, to determine the amount of fluid that has been delivered to the patient over a period of time.

When all of the air has thusly been removed, and the system is primed, the fluid itself will begin to exit from the tip 428 of the insertion needle 426, thereby signaling to the person using the device that the desired priming has been accomplished. Although it is not necessary due to the cylindrical segment 460 projecting from the bottom of the holding pad 412, the material from which the delivery tube 448, the catheter hub 440, and the retaining cap 442 are made may be transparent, to thereby provide means for visually determining whether all of the air bubbles have been removed from the delivery tube 448 and the fluid chamber 444.

Figure 16:
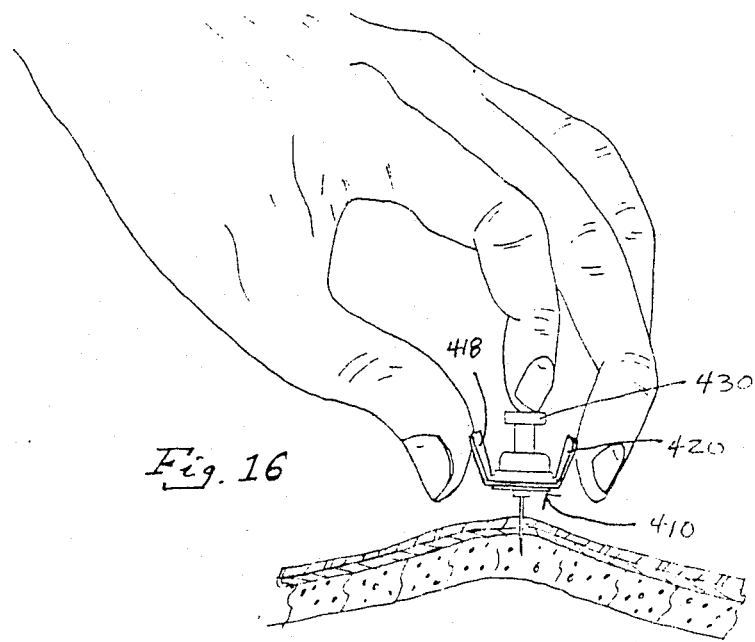
FIG. 16 is an illustration of the method used to insert the injection set of FIGS. 10–15 into the skin.

With all of the air thusly removed from the system, the injection set 410 may then be inserted into the patient in the same manner illustrated in FIG. 16. The wing portions 418, 420 of the holding pad 412 are bent upwardly between the thumb and the middle finger, with the index finger on the handle 430 of the insertion needle 426. The protective paper backing 434 is removed to expose the pressure-sensitive adhesive 432. The insertion needle 426 is inserted into the skin together with the soft cannula 414 until the bottom of the cylindrical segment 460 is in contact with the skin.

The reason for this cylindrical segment 460 protruding from the bottom of the holding pad 412, and the critical nature of the design, are now apparent. The visibility to the user is greatly increased, and the user can easily visually verify that the soft cannula 414 is fully inserted into the skin prior to removal of the insertion needle 426. This prevents the soft cannula 414 from kinking when the insertion needle 426 is removed. In addition, it will be appreciated that the cylindrical segment 460 will continue to exert pressure on the skin immediately around the insertion site, thereby maintaining the soft cannula 414 in the skin and continuing to prevent kinking of the soft cannula 414.

Figure 15:
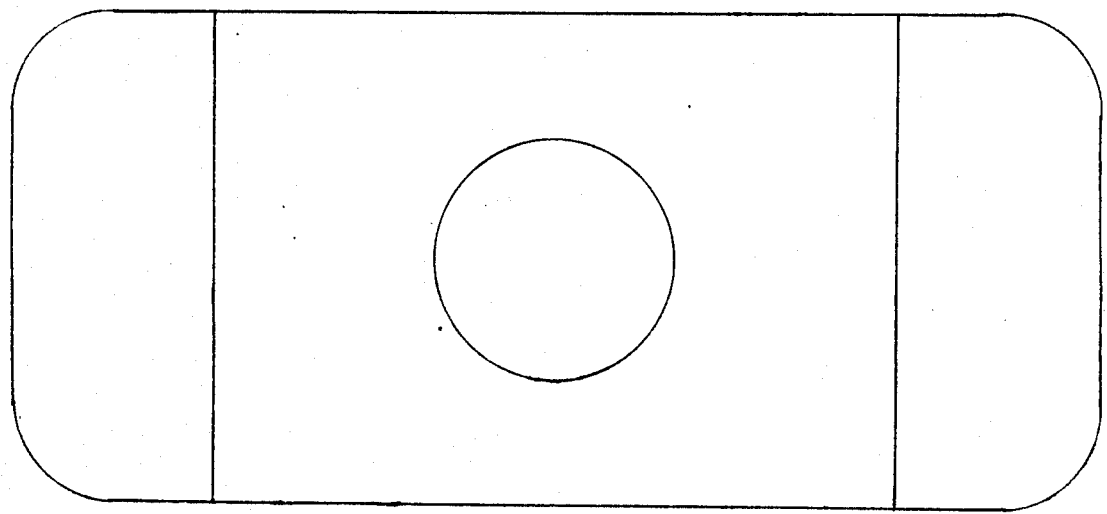
FIG. 15 is a plan view from the bottom of the adhesive patch used to retain the injection set of FIGS. 10 and 11 in place on the skin.

In the preferred embodiment, the injection set 410 is also retained by the use of an adhesive patch 470, shown in FIG. 15. The adhesive patch 470 is rectangular and has an aperture centrally located therein to admit the handle 430 and the largest circular protrusion on the top of the holding pad 412 as well as the catheter hub 440 and the retaining cap 442. The lines on the adhesive patch 470 indicate protective paper backing which is removed from the bottom surface of the adhesive patch 470. The adhesive patch 470 is then placed over the injection set 410 to retain it on the skin.

It will be appreciated that adhesive on the entire underside of the holding pad 412 could be used instead of the adhesive patch 470, but the adhesive patch 470 provides a more secure installation of the injection set 410.

The inner diameter of the lumen 446 is again typically approximately 24 gauge, and is the smallest opening associated with the delivery system. This lumen 446 allows appropriate amounts of fluid to be delivered under control of the infusion pump (not shown) without excessvie flow restriction. Since this delivery channel has the capacity to deliver relatively large volumes of fluid, what is again virtually a free flow subcutaneous delivery channel is provided once the injection set 410 has been put in place.

Because of the simplicity of the preferred embodiment of the injection set 410 described above, it is adaptable to use as a disposable device which may be conveniently used by the patient without need of medical assistance from a nurse or doctor. After appropriate usage, it may be discarded. A typical use of the injection set 410 will be by diabetics who receive a controlled dose of insulin from an external insulin infusion pump. The patient need only load the external infusion pump with the source of fluid and connect it to the injection set 410, prime the injection set 410, and then insert the injection set 410 at an appropriate skin location. This entire operation may be completed in a very short time period (e.g. less than 60 seconds). With the miniaturized external infusion pumps now available, and with the injection set as described herein, it is unlikely that anyone other than the patient will know or be able to determine that an infusion pump and injection set 410 are being used.

In addition, the preferred embodiment has the significant advantage that it allows simple visual verification of the fact that the soft cannula 414 has been fully inserted into the skin of the patient. This ensures that the soft cannula 414 will not kink when the insertion needle 426 is removed. In addition, since the cylindrical segment 460 will continue to exert pressure on the skin immediately around the insertion site, the soft cannula 414 will be maintained fully inserted into the skin, thereby continuing to prevent kinking of the soft cannula 414.

While the invention herein disclosed has been described by means of a specific preferred embodiment as well as several other embodiments and applications thereof, numerous modifications and variations could be made thereto by those skilled in the art without departing from the spirit and scope of the present invention. It is therefore to be understood that within the scope of the appended claims, the invention may be practiced otherwise than as specifically described herein.

What is claimed is:

1. A subcutaneous injection set comprising:
   a holding pad for placement on the skin of a patient at an injection site, said holding pad having an aperture therein;
   a catheter hub mounted on top of said holding pad, said catheter hub having a fluid chamber therein, said catheter hub also having a cylindrical segment extending through said aperture in said holding pad and extending below the bottom surface of said holding pad, said cylindrical segment having an aperture therethrough in communication with said fluid chamber;
   self-sealing means for enclosing said fluid chamber on the top of said catheter hub;
   means for receiving a desired fluid into said fluid chamber;
   a soft cannula mounted in and extending from said cylindrical segment of said catheter hub, said soft catheter having a lumen therethrough, said lumen being in fluid communication with said fluid chamber in said catheter hub;
   an insertion needle for removable insertion through said self-sealing means on said top of said catheter hub, said insertion needle passing through said fluid chamber and through said lumen of said soft cannula, said insertion needle having an outside diameter size which tightly fits and passes through the lumen of said soft cannula, a sharpened tip of said insertion needle extending beyond the length of said soft cannula when said insertion needle is fully inserted through said housing, said self-sealing means sealing said top of said catheter hub when said insertion needle is withdrawn therefrom; and
   means for removably securing said holding pad to the skin of a patient.

2. An injection set as defined in claim 1, wherein said holding pad comprises:
   a central portion from which said soft cannula protrudes; and
   two wing portions extending from opposite sides of said central portion, said two wing portions being connected to said central portion by two areas of reduced thickness which act as hinges to allow said two wing portions to move with respect to said central portion, thereby enabling said holding pad to fit to the contour rather well.

3. An injection set as defined in claim 2, wherein said holding pad is molded of flexible PVC.

4. An injection set as defined in claim 1, wherein said first self-sealing means comprises:
   a septum layer made from a pierceable, resilient, resealable substance; and
   a retaining cap which is affixed to said catheter hub over said septum thereby compressing said septum, said cap having a small aperture therethrough through which said insertion needle may be inserted.

5. An injection set as defined in claim 4, wherein said septum is made of medical grade silicone rubber.

6. An injection set as defined in claim 4, wherein said retaining cap has a raised circular sealing ring located on the inside of the top of said retaining cap and spaced away and around said aperture in said retaining cap, said raised circular sealing ring pressing into the top of said septum to enhance the sealing characteristics of said injection set.

7. An injection set as defined in claim 4, wherein said retaining cap is secured in place on said catheter hub by a raised snap ring which extends around the lower inside edge of the retaining cap, said retaining cap snapping onto said catheter hub.

8. An injection set as defined in claim 1, wherein said receiving means is so arranged and configured to deliver said fluid into said fluid chamber through the side of said catheter hub.

9. An injection set as defined in claim 1, wherein said soft cannula is made of teflon.

10. An injection set as defined in claim 1, wherein said soft cannula is made of hydrogel material.

11. An injection set as defined in claim 1, wherein the end of said soft cannula is tapered to enhance insertion of said soft cannula.

12. An injection set as defined in claim 1, further comprising:
   means for priming said injection set when said receiving means is connected to a source of fluid prior to insertion of said insertion needle and said soft cannula into the skin of a patient.

13. An injection set as defined in claim 12, wherein said priming means comprises:
   a passage between said sharpened tip of said insertion needle and a section of said insertion needle within said fluid chamber, said passage being in fluid communication with said fluid chamber, whereby all air or other gases within said fluid chamber may escape through said air passage when said sharpened tip of said insertion needle is held so as to point in an upwards direction as fluid is introduced under pressure into said fluid chamber through said receiving means.

14. An injection set as defined in claim 13, wherein said passage comprises:
   a bore located within said insertion needle; and
   an aperture from the exterior of said insertion needle to said bore, said aperture being located in said fluid chamber at a position near said first side of said housing when said insertion needle is fully inserted through said catheter hub.

15. An injection set as defined in claim 13, wherein said passage comprises a longitudinal groove disposed along the side of said insertion needle.

16. An injection set as defined in claim 15, wherein said receiving means includes a flexible tube in fluid communication with the fluid chamber within said catheter hub, said flexible tube exiting out through the side of said catheter hub at an angle substantially parallel to the skin said mounting pad is placed on.

17. An injection set as defined in claim 1, wherein said means for removably securing said holding pad to the skin of the patient comprises:
   an adhesive layer attached to the bottom side of said holding pad, said adhesive layer sticking to the skin of the patient as soon as contact is made between said other side of said adhesive layer and the skin.

18. An injection set as defined in claim 17 wherein said adhesive layer includes thereon an antimicrobial substance on the side of said adhesive layer facing the skin of the patient, which antimicrobial substance reduces the risk of infection as said injection set is used by the patient.

19. An injection set as defined in claim 17, wherein said other side of said adhesive layer is covered with a disposable covering which may be manually removed when said injection set is ready to be affixed to the skin of the patient, said disposable covering having an aperture therein through which said cylindrical portion of said catheter hub, said soft cannula, and said insertion needle pass, said disposable covering also having a slit which passes from said aperture to an outer edge of said disposable covering, said disposable cover further having a finger tab which projects out from said edge adjacent said slit, whereby said disposable covering may be pulled off of said adhesive by pulling said finger tab away from said first side of said housing with a circular motion which does not require lifting or sliding the disposable covering over said soft cannula or said insertion needle.

20. An injection set as defined in claim 17, wherein said means for removably securing said holding pad to the skin of the patient additionally comprises:
   a rectangular adhesive patch having an aperture centrally located therein for admitting said catheter hub, said rectangular adhesive patch having removable protective paper backing on the bottom surface thereof, said adhesive patch being placed over said holding pad after said removable protective paper backing has been removed to retain said injection set on the skin.

21. An injection set for injecting a desired fluid from a source of fluid to a subcutaneous delivery location under the skin of a patient, said injection set comprising:
   a holding pad for placement on the skin of a patient at an injection site, said holding pad having an aperture therein;
   a catheter hub mounted on top of said holding pad, said catheter hub having a fluid chamber therein, said catheter hub also having a cylindrical segment extending through said aperture in said holding pad and extending below the bottom surface of said holding pad, said cylindrical segment having an aperture therethrough in communication with said fluid chamber;
   self-sealing means for enclosing said fluid chamber on the top of said catheter hub;
   a flexible cannula having a first end affixed within said catheter hub and a second end which protrudes from said cylindrical segment of said catheter hub, said cannula having a lumen therein extending between said first and second ends, said lumen being in fluid communication with said fluid chamber in said catheter hub;
   a delivery tube having a first end affixed to said catheter hub, said delivery tube being substantially parallel to the skin of the patient as it approaches and is attached to said catheter hub, a second end of said delivery tube being connectable to said source of fluid;
   fluid connection means within said catheter hub for maintaining said first end of said delivery tube in fluid communication with said fluid chamber; and
   cannula insertion means for inserting the protruding body portion of the flexible cannula into the subcutaneous fat layer of the skin of the patient as the flat surface of the housing is placed against the skin of the patient.

22. An injection set as defined in claim 21, wherein said cannula insertion means comprises:

an insertion needle tightly inserted into said lumen of said cannula, a sharpened tip of said insertion needle projecting beyond said second end of said cannula when said insertion needle is fully inserted thereinto, said insertion needle having a means for gripping an end thereof opposite said sharpened tip, said means for gripping being accessible from the top of said catheter hub, whereby said sharpened tip of said needle punctures the skin and enters a subcutaneous fat layer of the patient as said holding pad is pushed against the skin of the patient, said second end of said cannula being carried into the subcutaneous fat layer with said needle, said needle being retractable from the lumen of said cannula once said second end of said cannula has been inserted into the subcutaneous fat layer.

23. An injection set for injecting a desired fluid from a source of fluid to a delivery location under the skin and in the subcutaneous fat layer of a patient, comprising:

a holding pad for placement on the skin of a patient at an injection site, said holding pad having a central portion with an aperture therein from which said soft cannula protrudes, said holding pad also having two wing portions extending from opposite sides of said central portion, said two wing portions being hingeably connected to said central portion by two areas of reduced thickness, thereby enabling said holding pad to fit to the contour rather well;

a catheter hub mounted on top of said holding pad, said catheter hub having a fluid chamber therein, said catheter hub also having a cylindrical segment extending through said aperture in said holding pad and extending below the bottom surface of said holding pad, said cylindrical segment having an aperture therethrough in communication with said fluid chamber;

a septum made from a pierceable, resilient, resealable substance, said septum enclosing said fluid chamber on the top of said catheter hub;

a retaining cap which is affixed to said catheter hub over said septum thereby compressing said septum, said cap having a small aperture therethrough through which said insertion needle may be inserted;

a flexible tube in fluid communication with the fluid chamber within said catheter hub, said flexible tube exiting out through the side of said catheter hub at an angle substantially parallel to the skin said mounting pad is placed on;

a soft cannula mounted in and extending from said cylindrical segment of said catheter hub, said soft catheter having a lumen therethrough, said lumen being in fluid communication with said fluid chamber in said catheter hub;

an insertion needle for removable insertion through said self-sealing means on said top of said catheter hub, said insertion needle passing through said fluid chamber and through said lumen of said soft cannula, said insertion needle having an outside diameter size which tightly fits and passes through the lumen of said soft cannula, a sharpened tip of said insertion needle extending beyond the length of said soft cannula when said insertion needle is fully inserted through said housing, said self-sealing means sealing said top of said catheter hub when said insertion needle is withdrawn therefrom; and means for removably securing said holding pad to the skin of a patient.

* * * * *